(12) United States Patent
Tian

(10) Patent No.: US 12,083,009 B2
(45) Date of Patent: Sep. 10, 2024

(54) METHOD OF PROCESSING COLLAGEN-BASED TISSUE FOR BIOPROSTHETIC DEVICES

(71) Applicant: Vitae LLC, Irvine, CA (US)

(72) Inventor: Bin Tian, Irvine, CA (US)

(73) Assignee: Vitae LLC, Irvine, CA (US)

( * ) Notice: Subject to any disclaimer, the term of this patent is extended or adjusted under 35 U.S.C. 154(b) by 499 days.

(21) Appl. No.: 16/849,694

(22) Filed: Apr. 15, 2020

(65) Prior Publication Data

US 2021/0322154 A1 Oct. 21, 2021

(51) Int. Cl.
*A61L 27/36* (2006.01)
*A61F 2/24* (2006.01)
*C12N 5/071* (2010.01)
*C12N 5/077* (2010.01)

(52) U.S. Cl.
CPC ........ *A61F 2/2415* (2013.01); *A61L 27/3604* (2013.01); *A61L 27/3625* (2013.01); *A61L 27/3641* (2013.01); *A61L 27/3687* (2013.01); *A61L 27/3691* (2013.01); *C12N 5/0657* (2013.01); *C12N 5/0697* (2013.01); *A61L 2430/20* (2013.01); *A61L 2430/40* (2013.01)

(58) Field of Classification Search
CPC ............. A61L 27/3625; A61L 27/3641; A61L 27/3687; A61L 2430/20; A61L 2430/40
See application file for complete search history.

(56) References Cited

U.S. PATENT DOCUMENTS

| | | | |
|---|---|---|---|
| 5,862,806 A * | 1/1999 | Cheung | A61L 27/3683 8/94.11 |
| 6,008,292 A | 12/1999 | Lee et al. | |
| 6,214,054 B1 | 4/2001 | Cunanan et al. | |
| 6,231,608 B1 | 5/2001 | Stone | |
| 6,471,723 B1 | 10/2002 | Ashworth et al. | |
| 6,509,145 B1 | 1/2003 | Torriani | |
| 6,547,827 B2 | 4/2003 | Carpentier et al. | |
| 7,029,434 B2 | 4/2006 | Carpentier et al. | |
| 7,214,344 B2 | 5/2007 | Carpentier et al. | |
| 7,579,381 B2 | 8/2009 | Dove | |
| 7,622,276 B2 | 11/2009 | Cunanan et al. | |
| 8,007,992 B2 | 8/2011 | Tian et al. | |
| 8,236,241 B2 | 8/2012 | Carpentier et al. | |
| 8,822,219 B2 | 9/2014 | Strasly et al. | |
| 9,351,829 B2 | 5/2016 | Carpentier et al. | |
| 9,402,934 B2 | 8/2016 | Rzany et al. | |
| 9,457,130 B2 | 10/2016 | Strasly et al. | |
| 9,968,447 B2 | 5/2018 | McKinley et al. | |
| 10,188,511 B2 | 1/2019 | Dove et al. | |
| 10,299,916 B2 | 5/2019 | Tien et al. | |
| 10,390,946 B2 | 8/2019 | Lehenberger et al. | |
| 10,434,218 B2 | 10/2019 | Davidson et al. | |
| 10,537,662 B2 | 1/2020 | Rzany et al. | |
| 2011/0165676 A1 | 7/2011 | Hopkins | |
| 2011/0311493 A1 | 12/2011 | Dove et al. | |
| 2012/0035720 A1* | 2/2012 | Cali | B23K 26/324 623/2.16 |
| 2017/0227430 A1* | 8/2017 | Marini | G01N 1/30 |
| 2017/0319357 A1 | 11/2017 | Wolfinbarger, Jr. et al. | |

FOREIGN PATENT DOCUMENTS

WO  WO198401879 A1 *  5/1984  ............... A01N 1/00

OTHER PUBLICATIONS

International Search Report dated Jul. 22, 2021 for corresponding PCT Application No. PCT/US21/26264.

* cited by examiner

*Primary Examiner* — Taeyoon Kim
(74) *Attorney, Agent, or Firm* — Raymond Sun

(57) ABSTRACT

A method is provided for preparing pericardial tissue that is used for a bioprosthetic heart valve assembly. According to this method, pericardial tissue is harvested from a host animal and then cleaned. The cleaned tissue is then fixed using glutaraldehyde. After fixation of the tissue, the residual antigenic components are removed to preserve the tissue structural integrity for its long-term performance. In addition, higher concentrations of alcohol are used to reduce the tissue bioburden, and at the same time to dehydrate the tissue followed by preserving the tissue with glycerol so as to mitigate glutaraldehyde-storage related issues for the bioprosthetic heart valve.

4 Claims, 5 Drawing Sheets

- Compared with Glut Fixed or Post Rehydration group p<0.05. No significant differences between Glut Fixed or Post Rehydration groups.

METHOD OF PROCESSING COLLAGEN-BASED TISSUE FOR BIOPROSTHETIC DEVICES

BACKGROUND OF THE INVENTION

1. Field of the Invention

The present invention is directed to a novel tissue processing technology that treats biological tissue including but not limited to pericardial tissue for applications in bioprosthetic heart valves (BHV) and cardiovascular or other tissue repair. The tissue treatment technology of the present invention aims to eliminate or reduce the leaflet tissue calcification and mitigates other host reactions against the bioprostheses by reducing the residual glutaraldehyde, and removing lipids/fat and antigenic materials that could not be masked by glutaraldehyde alone.

2. Description of the Prior Art

Glutaraldehyde fixed bovine or porcine pericardium has been used as leaflet material for BHVs since the 1980s, and demonstrated to have reasonably good clinical outcome. In addition to surgically implanted pericardial BHVs, trans-catheter-delivered heart valves (THV) also use pericardium as leaflet material and have become standard care for non-operable, high risk patients, and intermediate risk patients who suffered from aortic stenosis. However, all BHVs have limited longevity after implantation in patients due to two major reasons: (i) unlike the native living heart valve, the BHV lacks self-repair in response to damages owing to the wear and tear; and (ii) bioprosthetic leaflet tissue calcification related structural valvular deterioration (SVD) and other non-calcific SVD can significantly shorten device longevity. In fact, leaflet tissue calcification related SVD is still the number one chronic failure mode for the BHV regardless of the brand, model, or manufacturer. Although the detail mechanisms of bioprosthetic calcification are not fully understood, it is believed that the chemical, specifically the glutaraldehyde, used to preserve the leaflet tissue is one of major contributing factors leading to the tissue calcification.

Tremendous efforts were made by heart valve producers to mitigate the glutaraldehyde toxicity related SVD due to the tissue calcification. Almost all newer generations of BHV claimed to have incorporated certain types of anti-calcification treatment, mostly by trying to reduce the glutaraldehyde toxicity. These efforts, however, appear to have only some limited clinical efficacy as the leaflet tissue calcification remains to be the major chronic failure mode. These clinical observations raise the question about the role of so-called "residual glutaraldehyde" in the calcification in bioprosthetic heart valves post implant. In fact, a vast majority of tissue calcification occurred years after the implantation, suggesting that the calcification may be related to the patient's biological factors. This is because, if residual glutaraldehyde is the major factor triggering bioprosthetic leaflet tissue calcification, one would expect all of the heart valves implanted in patients to be calcified sooner and this should occur in all of the implants. Unfortunately, the clinical data showed that the occurrence of bioprosthetic heart valve calcification can range from months to more than ten years, suggesting residual glutaraldehyde is neither a major contributor nor an initiator for bioprosthetic heart valve calcification in patients. At the same time, residual and free glutaraldehyde present in BHVs related to the storage of the devices in the glutaraldehyde-containing solutions may trigger inflammatory response upon the implant that may contribute to the host tissue overgrowth.

Despite all of the above-mentioned disadvantages of using glutaraldehyde to fix the bioprosthetic tissue, glutaraldehyde is in fact the most important discovery in bioprosthetic heart valve history because glutaraldehyde played a crucial role in reducing host immune response against the bioprosthesis by masking the antigens in the xenogeneic tissue through cross-linking, and significantly improving the longevity of the bioprosthesis by providing a superior preservation of the tissue. On the other hand, accumulating information suggests that the antigenicity of the xenogeneic tissue was not completely masked by the glutaraldehyde fixation. This probably explained why the strategies that focused solely on glutaraldehyde detoxication have limited clinical efficacy from the anti-leaflet tissue calcification perspective. Therefore, it appears that the calcification and other failure modes observed in BHVs are probably attributable to the host response to those non-living materials, especially the immunogenicity of the tissue used to build the heart valves. So far, most of the anti-calcification strategies have been focused on decreasing the toxicity of the glutaraldehyde. Very few efforts were made to effectively address the antigenicity of the leaflet tissue itself (i.e., the animal tissue used to build the BHV), especially post-leaflet tissue fixation.

Thus, the present invention is directed towards the objectives of (i) removing the tissue antigenicity after glutaraldehyde fixation; and (ii) treating the heart valve with a reversible tissue dehydration technology and storing the heart valve in a non-liquid form.

SUMMARY OF THE DISCLOSURE

In order to accomplish the objects of the present invention, there is provided a method for preparing pericardial tissue that is used for a bioprosthetic heart valve assembly. According to this method, pericardial tissue is harvested from a host animal and then cleaned. The cleaned tissue is then fixed using glutaraldehyde. After fixation of the tissue, lipids/fat and residual antigenic components are removed, and then tissue bioburden is reduced.

In accordance with one embodiment of the present invention, the step of removing lipids/fat and residual antigenic components includes treating the tissue with a solution consisting of alcohol (20% to 70%) and Tween-20 (0.1% to 1%) in buffered saline (pH 7.0-7.5) at 30° C. to 60° C. for 1 to 24 hours, and further includes treating the tissue with detergent solutions (0.1% to 1%) containing one or more of the following detergents: Sodium Deoxycholate (SDC), Sodium dodecyl sulfate (SDS), 3-[N,N-Dimethyl(3-myristoylaminopropyl)ammonio]propanesulfonate, Amidosulfobetaine-14 (ASB-14), 3-[(3-cholamidopropyl)dimethylammonio]-1-propanesulfonate (CHAPS). In addition, the step of reducing tissue bioburden uses 65% to 75% alcohol to reduce the tissue bioburden.

The pericardial tissue prepared by this method can be used to make a bioprosthetic heart valve assembly. After the tissue has been prepared according to this method, the heart valve can be assembled. As part of the assembly, the glutaraldehyde is detoxified from the treated tissue of the leaflets, and reversible tissue dehydration (RTD) is applied by dehydrating the tissue using 60% to 95% of alcohol for one to eight hours at 25° C. to 55° C., and then treating the tissue with a mixture solution consisting of glycerol (80% to 95%), ethanol (5% to 10%), and deionized water (3% to 10%) at room temperature for 30 minutes to 24 hours.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Figure 1:
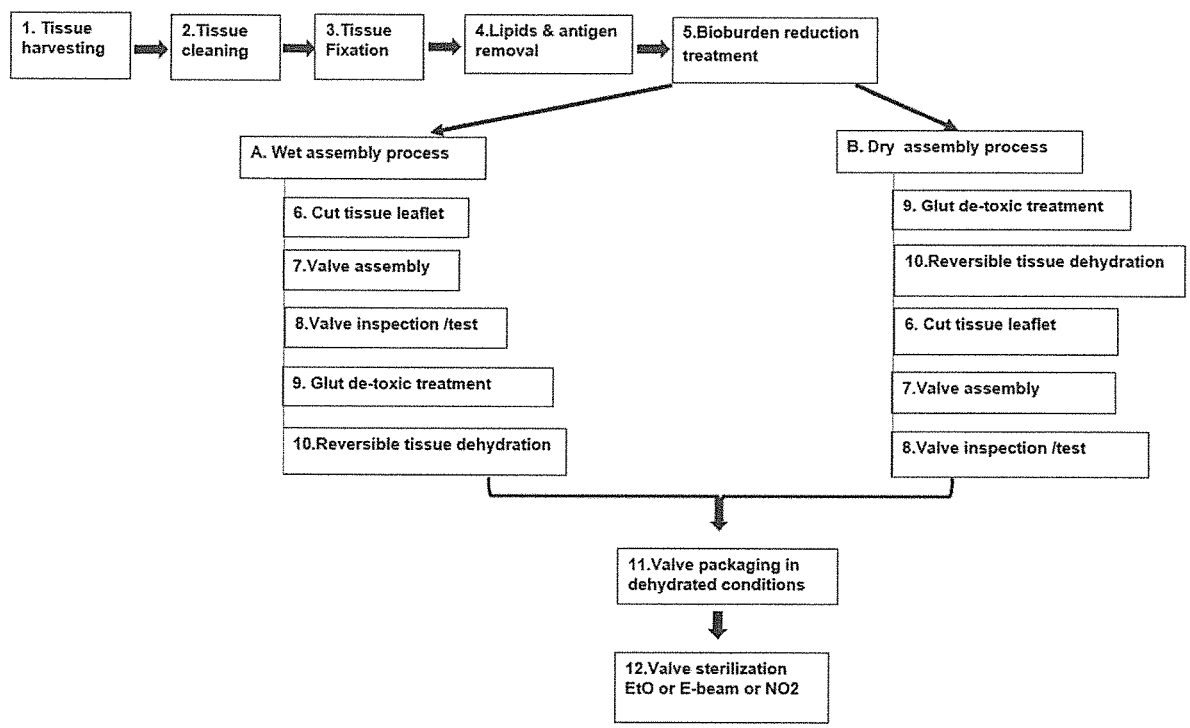
FIG. 1 is a flow chart illustrating the process according to one embodiment of the present invention.

The inventive tissue process according to one embodiment of the present invention is illustrated in the flow chart of FIG. 1. Even though the process is described in connection with a bioprosthetic heart valve, it is also possible to apply this process to other valves and bioprosthetic devices.

Tissue Harvesting

Pericardial tissue is a collagen-rich fibrous connective tissue wrapped around the heart. During the tissue harvesting step (step 1), the pericardial sac, which is a "half-football" like bag, is removed from the heart of the host animal by detaching it from large vessels at the base of the heart from where it is originated. After the outside layer of adipose/fat tissue has been peeled off, the fibrous membrane pericardial sac is rinsed with water, preferably with cold normal saline (0.9% sodium chloride). The sacs are then collected in plastic bags containing cold saline and shipped to the manufacturer for further processing. Typically, the tissue should be processed within 72 hours after harvesting.

Tissue Cleaning

In step 2, the tissue cleaning process in manufacture (at the tissue processing center) is started upon receipt. The pericardial sac is first cut and flattened out. Tissue is inspected for any pathological defect. The tissue is then trimmed into a relatively regular patch, usually a rectangular shape, and additional adipose or other loose tissue on the surface is carefully removed. The tissue is then washed/rinsed with cold normal saline to remove any residual blood a or tissue debris.

Tissue Fixation

The tissue is then fixed in step 3. Using glutaraldehyde (hereinafter also referred to as "Glut") to fix xenogeneic tissue for bioprosthetic heart valves (BHV) is probably one of the major innovations in cardiovascular surgical history. Glut was initially used to fix tissue samples for pathology analysis. Approximately fifty years ago, Glut was used to preserve/fix bioprosthetic tissue for BHV applications and has been proven to be the most effective tissue fixative in BHV history. Many other alternative fixatives such as EDC and genipin have been tried and so far there is no better way to preserve the BHVs than Glut.

Figure 2:
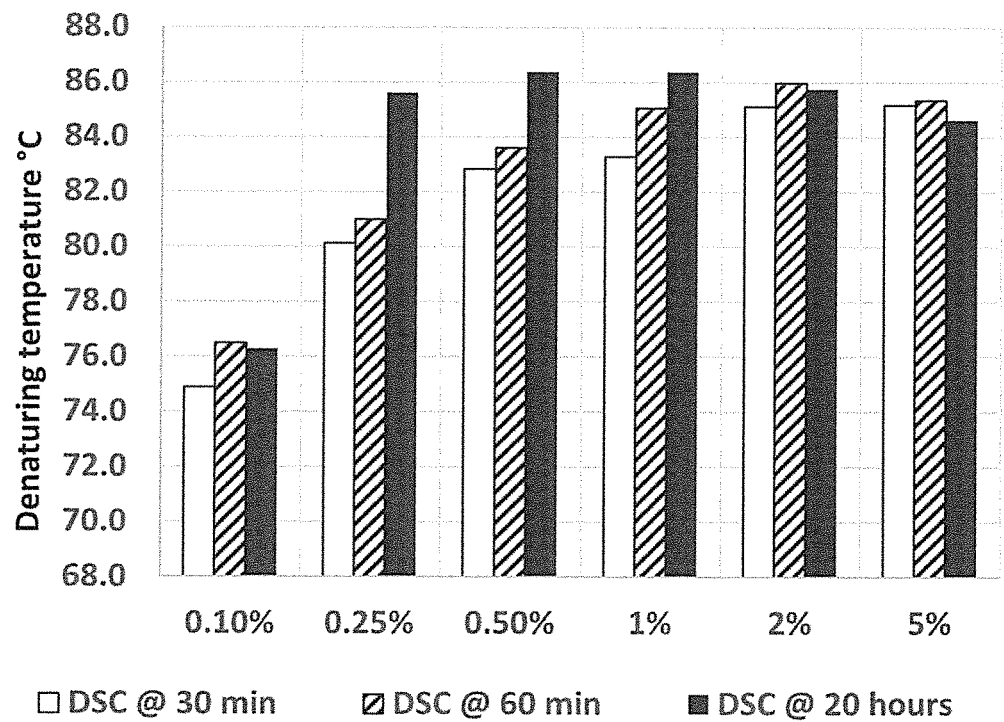
FIG. 2 is a chart that illustrates the effect of glutaraldehyde concentration and fixation time on tissue cross-linking by DSC (differential scattering calorimetry).

Glutaraldehyde consists of two aldehyde groups and is highly active. Glut tissue is fixed by cross-linking the amine group of the amino acids in an irreversible fashion. Glut can work in a wide range of concentrations, ranging from 0.1% to more than 2%. Most BHV manufacturers use 0.25% to 0.625% of Glut in buffered phosphate saline (PBS) solution. Several factors dictate the effects of tissue cross-linking, including the Glut concentration, fixation time, temperature, solution pH, and purity of the Glut. As there is no feasible direct measurement of tissue cross-linking by Glut, several indirect methods such as tissue shrinkage temperature and differential scattering calorimetry (DSC) have been used to determine the status of tissue cross-linking. Typically, an effectively cross-linked tissue (pericardium) has an initial denaturing temperature approximately 84±3° C. by DSC, while the non-fixed fresh (pericardium) tissue is approximately 64° C. It is believed that using higher concentrations is not desirable due to the concern of the so-called "walling-off" effect that the edge of the tissue is cross-linked too quickly and could prevent the penetration of Glut into the inner site of the tissue. The inventor's work has also demonstrated that there is no appreciable difference in tissue cross-linking from 0.25% to 5% of Glut solutions for fixation for up to 20 hours at room temperature (see FIG. 2). Although the tissue denaturing temperature by DSC showed that there is concentration dependency with the tissue (porcine pericardium) fixation for 30 minutes, this concentration-dependent difference diminished at 20 hours post-fixation for the concentration of 0.25% or higher, as evidenced by the denaturing temperature reached plateau. Therefore, using Glut concentrations between 0.25% to 1% is adequate if the fixation time is more than 24 hours from the time of tissue fixation/preservation.

Lipids and Antigen Removal

Lipids and antigen are removed in step 4. It is well-known that any xenogeneic tissue cannot be directly implanted into human body because of the immune rejection. Glut fixation has been shown to significantly reduce the immune response against the xenogeneic tissue containing devices such as BHVs by unmasking the antigens presented in the tissue. As mentioned previously, one of the major challenges is the longevity of Glut-fixed BHVs is calcific and non-calcific SVD. It was previously believed that the toxicity from the Glut is the primary factor causing the leaflet tissue calcification in BHVs. However, now it has become clear that simply reducing or eliminating the Glut toxicity may not be enough. Other potential factors such as lipids/fat and antigens that are not sufficiently unmasked by the Glut-fixation could play an important role in SVD related to both calcific and non-calcific manners. In fact, many methods have been developed to remove the cells and antigens from the xenogeneic tissue prior to the fixation. However, all of these approaches have one major disadvantage in that the tissue treatments can damage/alter the tissue structure. The de-celled tissue usually becomes thicker due to the loosened collagen fibers, and the typical fibrous structure becomes somewhat amorphous in some instances. These structural changes may have an impact on tissue integrity and long-term durability.

In fact, at this time, there is no known bioprosthetic heart valve in the market that is made from the above-mentioned de-cell or removal of antigenicity treatment. This is because these tissue treatments were usually performed directly to the fresh tissue prior to the fixation, resulting in permanent structural tissue damage, such as micro or macro tissue delimitation, tissue degradation, loosening of collagen bundles etc. These undesirable structural changes render the resultant tissue to be unusable as BHV leaflet material.

In contrast, the present invention removes the lipids/fat and the residual antigenic components after the initial irreversible Glut-fixation. Specifically, the tissue will be treated with a solution consisting of alcohol (20% to 70%) and detergent such as Tween-20 (0.1% to 1%) in buffered saline (pH 7.0-7.5) at 30° C. to 60° C. for 1 to 24 hours. Preferably, the solution consists of 30% ethanol or isopropanol and 0.25% Tween-20 at 45±2° C. and treatment is for 2 hours. Subsequently, the tissue is treated with detergent solutions (0.1% to 1%) containing one or more of the detergents, including but not limited to Sodium Deoxycholate (SDC), Sodium dodecyl sulfate (SDS), 3-[N,N-Dimethyl(3-myristoylaminopropyl)ammonio]propanesulfonate, Amidosulfobetaine-14 (ASB-14), 3-[(3-cholamidopropyl)dimethylammonio]-1-propanesulfonate (CHAPS). Preferably, the tissue will be treated with a combination of 0.5% of SDC and 0.25% ASB-14. As the tissue will be fixed with Glut solution before the removal of lipids and antigenicity, the structural integrity of the tissue will be preserved so as to make the tissue more biologically-compatible, and at the same time, preserve the mechanical properties for a long-lasting performance.

Bioburden Reduction

Bioburden reduction treatment is step 5. Bioburden in animal tissue is defined as any pathogens such as bacteria, fugus, virus, or other organism that is present in tissue. Because the tissue (such as pericardium) is harvested from healthy animals which are slaughtered for meat for human consumption, the tissue before harvesting is supposed to be clean. In most cases, the pathogens originate from contaminations during the slaughtering, tissue harvesting, tissue shipment, and tissue processing. Upon harvesting, the tissue should be kept, stored, and shipped in cold normal saline to minimize the growth of the pathogens and to prevent tissue degradation. The reduction of bioburden starts from washing the tissue with clean normal saline and subsequent fixation with Glut solution. As pathogens are living organisms, they can be inactivated by fixatives such as Glut through cross-linking their protein and nucleic acids. Therefore, in addition to tissue preservation, Glut is also used as a disinfectant. However, the typical concentrations used to fix the bioprosthetic tissue is not strong enough to sterilize the tissue. Additional steps are taken to reduce the bioburden. Most common approaches include using the combination of formaldehyde, detergent, and alcohol, or a combination of Glut and alcohol, to further reduce the bioburden. However, formaldehyde is considered to be a highly hazardous material with carcinogenic risk, while Glut and alcohol may trigger chemical reactions that may compromise its efficacy.

Therefore, the present invention uses high concentrations of alcohol to reduce the tissue bioburden. Specifically, the present invention uses 65% to 75% alcohol to reduce the bioburden. The common concern for using higher concentrations of alcohol is that it may cause tissue dehydration that may result in permanent changes in tissue property.

Figure 3:
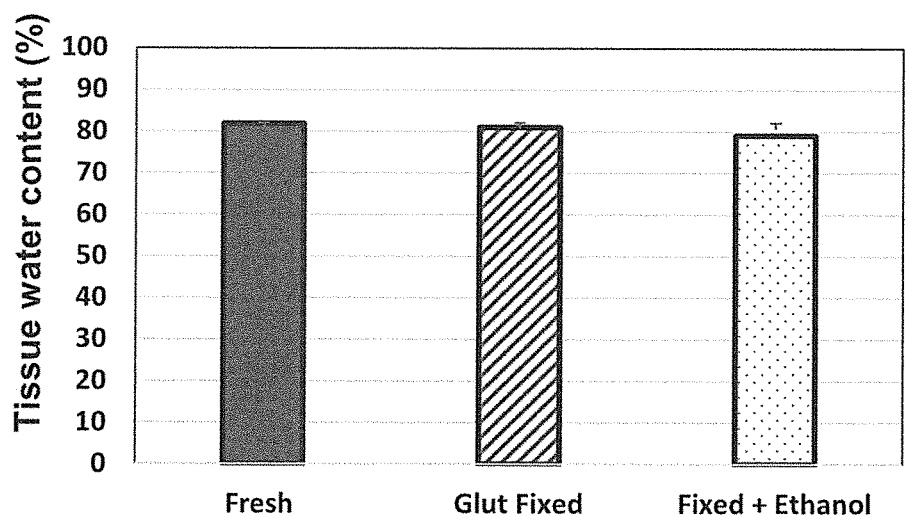
FIG. 3 is a chart that illustrates the effect of glutaraldehyde and ethanol on tissue water content.
Figure 4:
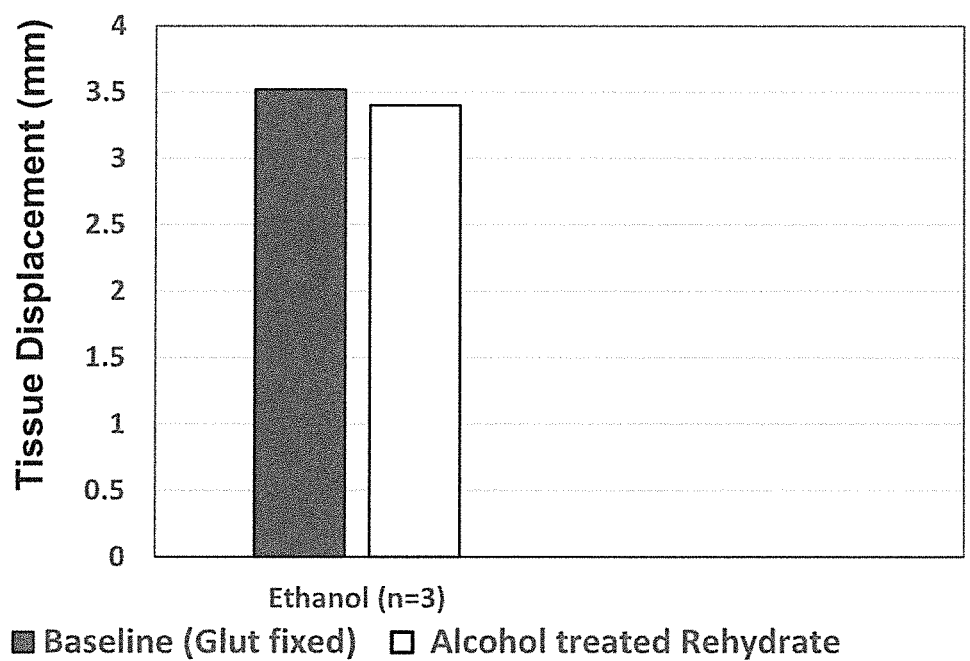
FIG. 4 is a chart that illustrates the effect of ethanol (70%) on tissue flexibility.

The inventor's recent experiments demonstrate that dehydration by the above-mentioned alcohol concentrations is reversible; this was demonstrated by tissue water content (see FIG. 3) and a tissue flexibility test (FIG. 4). It is well-known that Glut-fixed pericardial tissue contains approximately 80% of water by weight. From the water content perspective, the pericardial tissue can be considered as a "sponge-like" material. The water content plays a crucial role for maintaining some of the important mechanical properties, such as compressibility (important for THVs during valve crimping), flexibility etc. The inventor's experiment demonstrated that the alcohol treatment did not impair the tissue rehydration, suggesting the dehydration by alcohol treatment is reversible as shown in FIG. 3. At the same time, as functional measurement, that the tissue flexibility of alcohol-treated tissue is comparable with tissue before the treatment, demonstrating that the alcohol treatment has no detrimental effect on the tissue flexibility, which is one of the most important mechanical features as a valve leaflet material (FIG. 4). Therefore, using the alcohol concentration ranges described above is feasible for bioburden reduction. The disinfection/sterilization efficacy of alcohol has been well-established. The typical concentration is 70% to 75%. The rationale is that alcohol at an appropriate concentration can fix/precipitate the proteins and dehydrate the organism/tissue at the same time. The fixation may not as stable as the other fixatives such as Glut. However, if the fresh tissue is treated with alcohol prior to fixation by Glut, permanent tissue damage may occur, After step 5 (bioburden reduction), the method of the present invention is divided into two possible paths:

A. A wet assembly process that is defined by the tissue being processed in liquid, including the heart valve assembly. The Glut detoxication (step 9) and reversible tissue dehydration (RTD) treatment (step 10) will be applied after the heart valve is assembled. According to this path, the leaflet tissue should be kept in solution or with sufficient moisture to prevent the leaflets being permanently drying out.

B. A dry assembly process that is defined by the tissue first being treated with Glut detoxication (step 9) and RTD technology (step 10) prior to the assembly of the heart valve. According to this path, the heart valve will be kept in a dehydrated format.

The steps used in these two paths are similar, but are applied in different sequence. The major differences are: (1) for the wet valve assembly (Path A), the tissue is processed in aqueous solution or keep the tissue well-hydrated until RTD treatment in Step 10. Typically, the tissue may not be exposed to air for more than 10 minutes at any given single step to prevent the tissue from permanent dehydration; (2) for the dry assembly process (Path B), the tissue has to be processed in a "dry" format in air (cannot be re-exposed to any water-based aqueous solution) after the tissue has been treated with the RTD process. The tissue from this point can be treated like a "cloth" material from cutting the leaflets, valve assembly, to packaging.

Cut the Leaflet

Step 6: Bioprosthetic heart valve leaflets from pericardium can be cut out using a die cutter or using a laser machine. In the present invention, the leaflet can be cut out on the wet tissue for Path A, or cut on the dehydrated tissue for Path B.

Valve Assembly

Step 7: The heart valve can be assembled using the wet leaflet tissue (Path A) or cut on the dehydrated tissue (Path B).

Valve Inspection and Test

Step 8: After the completion of the heart valve assembly, the heart valve assembly is inspected for leaflet coaptation, or any other defects. Ideally, a functional testing should be performed to assess the immediate functionality, including leaflet opening/closing, coaptation, etc.

Glut Detoxication

Step 9: For a long time, the potential toxicity of Glut has been considered a major contributor to leaflet tissue calcification in BHVs. Therefore, most current anti-calcification strategies are focused on detoxication of the Glut, such as so-called capping chemicals (such as sodium borohydride treatment), or using animal acids to neutralize the free Glut. However, the claims on the effect of these detoxication treatments are largely based on the animal implants and need to be confirmed by long-term clinical studies. Nevertheless, free Glut in the final device can be problematic because Glut is highly reactive and can trigger local inflammatory response, especially since the majority of current BHVs are stored in solutions containing either Glut or formaldehyde. Therefore, in the present invention, the tissue/heart valve is washed adequately with normal saline, preferably containing 0.5% to 1% glycine or other amine containing amino acids in a volume ratio of 1:10 time (valve:solution) at room temperature with agitation (30 to 70 rpm) for 30 min to 60 min. This step is preferably to be repeated two to three times. Although it is possible that washing the tissue intensively with the saline as mentioned above might be sufficient to remove the free residual Glut in the tissue, the addition of amino acids could reduce any free residual Glut and neutralize the un-cross-linked aldehyde ends.

RTD Tissue Treatment

Figure 5:
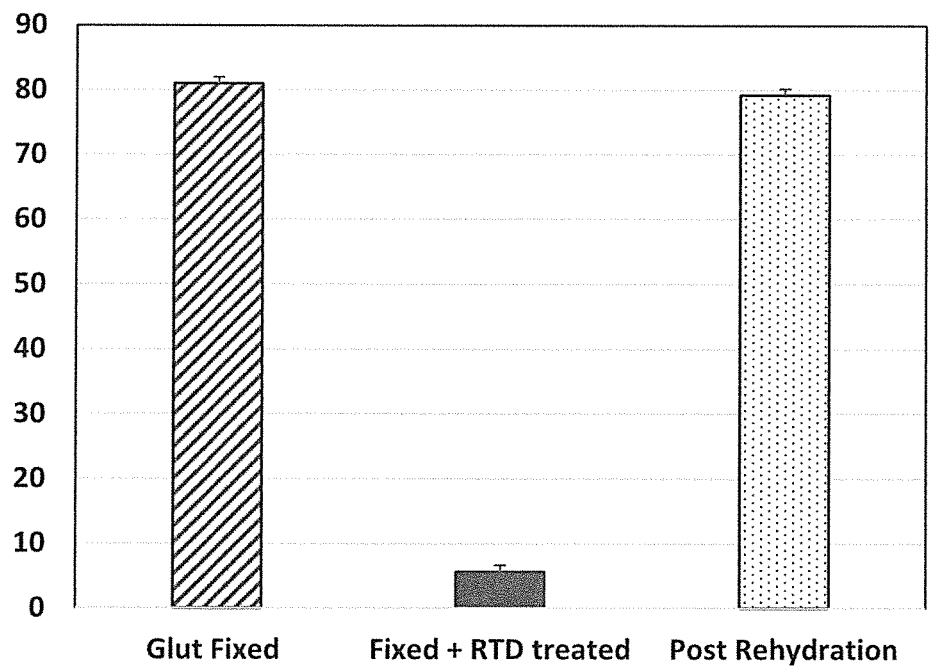
FIG. 5 is a chart that illustrates the effect of RTD (reversible tissue dehydration) treatment on tissue water content before and after rehydration.
Figure 6:
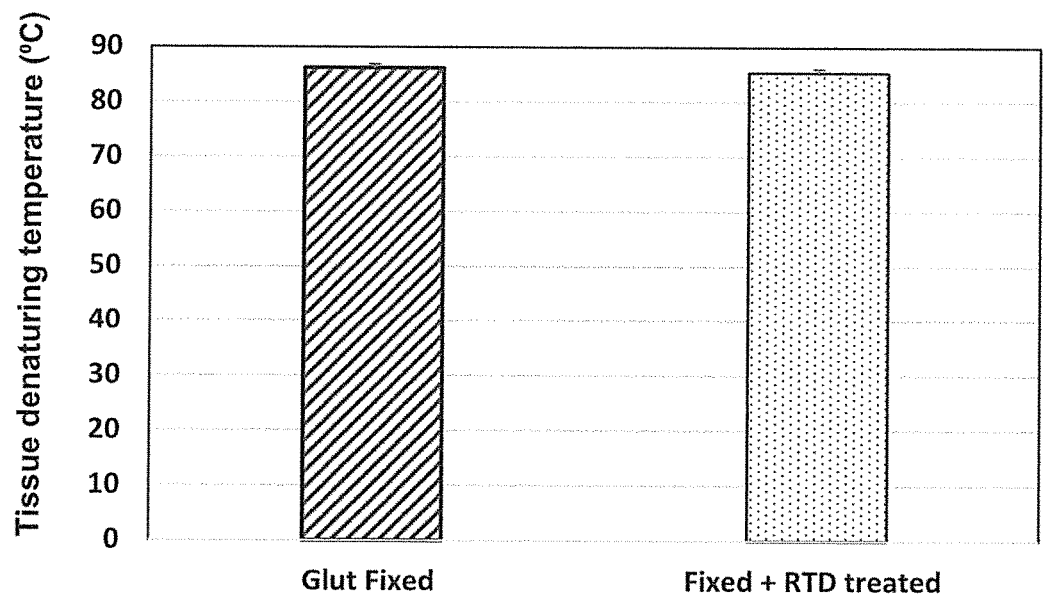
FIG. 6 is a chart that illustrates the change in tissue denaturing temperature in RTD treated tissue.
Figure 7:
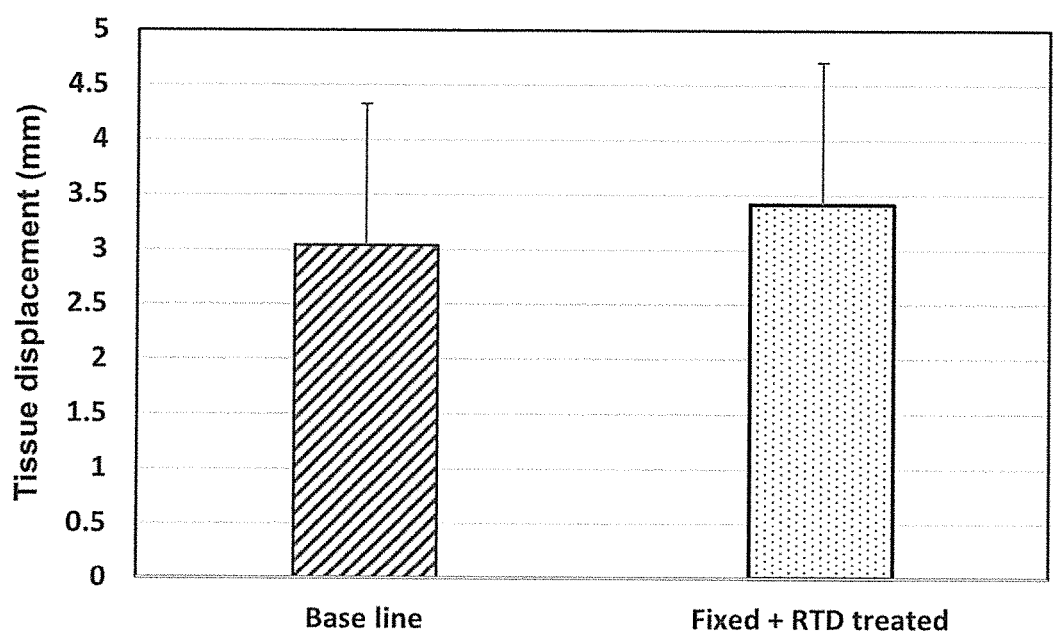
FIG. 7 is a chart that illustrates the effect of RTD treatment on tissue flexibility.

Step 10: Reversible tissue dehydration (RTD) according to the present invention is accomplished by dehydrating the pre-fixed tissue using alcohol followed by preservation with glycerol solution. Specifically, the tissue will be dehydrated using 60% to 95% of alcohol for one to eight hours at 25° C. to 55° C., preferably with 75% ethanol for two hours at 40° C. Then the tissue will be treated with a mixture solution consisting of glycerol (80% to 95%), ethanol (5% to 10%), and deionized water (3% to 10%) at room temperature for 30 minutes to 24 hours. Preferably, the tissue is treated with the mixture of 90% glycerol, 7% ethanol, and 3% deionized water at room temperature for 2 hours. Then the excessive chemicals will be removed by using non-fiber cloth manually and/or in conjunction of using a customized fixture to remove the excessive chemicals on the valve prior to the manual procedure. The inventor's experiment results demonstrated that the tissue treated with the above-mentioned solution can substantially dehydrate the tissue and the tissue is completely reversible upon rehydration with normal saline at room temperature. See FIG. 5, which shows the water content in the same pieces of tissue after Glut fixation, treated with the RTD process of the present invention, and then after rehydration in saline. The tissue water content as designed/expected is significantly lower ($p<0.05$) after the tissue is treated with the RTD process of the present invention compared to the tissue before the treatment or after the rehydration, demonstrating that the RTD treatment is fully reversible in terms of tissue water content. Additionally, there are no significant changes in tissue cross-linking (by denaturing temperature using DSC) or tissue flexibility in pre-fixed porcine pericardium treated with the RID technology of the present invention (See FIGS. 6 and 7). These experiment results demonstrated that, in addition to the reversible dehydration that can prevent the tissue's re-exposure to chemical-based liquid storage, an additional benefit of the present invention's RTD tissue treatment is to reduce the bioburden in the tissue resulting from higher concentrations of alcohol and possibly further reduce any residual lipids/fat in the tissue.

Unlike pre-existing methods, the present invention removes the residual antigenic components after the initial tissue fixation to preserve the tissue structural integrity for its long-term performance. In addition, the present invention uses higher concentrations of alcohol to reduce the tissue bioburden, and at the same time to dehydrate the tissue followed by preserving the tissue with glycerol so as to mitigate Glut-storage related issues for the bioprosthetic heart valve.

The comprehensive tissue processing method in this invention is expected to improve the current bioprosthetic heart valve to the next level as the proposed processes address the most challenging issues encountered by current bioprostheses in the market. These challenges include tissue calcification related to host immune response to the residual unmasked antigenicity, residual cellular and extracellular lipids/fat, and Glut toxicity. At the same time, the present invention minimizes the micro and macro tissue structural damages, thereby maximizing the mechanical durability of the valve leaflets and the bioprosthetic heart valve.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method for preparing a collagen-based pericardial tissue that is used for a bioprosthetic heart valve assembly, comprising:
   a) harvesting a pericardial tissue from a host animal;
   b) cleaning the harvested tissue;
   c) fixing the cleaned tissue using glutaraldehyde;
   d) treating the fixed tissue with a solution consisting of 20% to 70% alcohol and 0.1% to 1% polysorbate 20 in pH 7.0-7.5 buffered saline at 30° C. to 60° C., wherein the alcohol is either ethanol or isopropanol;
   e) treating the treated tissue from the step d) with a 0.1% to 1.0% detergent solution containing one or more of the following detergents: sodium deoxycholate (SDC), sodium dodecyl sulfate (SDS), 3-[N,N-Dimethyl(3-myristoylaminopropyl)ammonio]propanesulfonate, amidosulfobetaine-14 (ASB-14), 3-[(3-cholamidopropyl)dimethylammonio]-1-propanesulfonate (CHAPS); and
   f) treating the treated tissue from the step e) using 65% to 75% alcohol, wherein the alcohol is either ethanol or isopropanol.

2. The method of claim 1, wherein the detergent solution of the step e) is a combination of 0.5% of SDC and 0.25% ASB-14.

3. The method for making a bioprosthetic heart valve assembly of claim 1, wherein the method further comprising:
   g) cutting leaflets from the treated tissue of the step f) of claim 1;
   h) assembling the heart valve assembly using the cut leaflets;
   i) detoxifying the glutaraldehyde from the leaflets in the heart valve assembly;
   j) dehydrating the leaflets in the heart valve assembly using 60% to 95% of alcohol for one to eight hours at 25° C. to 55° C., wherein the alcohol is either ethanol or isopropanol; and
   k) treating the leaflets in the heart valve assembly with a solution consisting of 80-90% glycerol, 5-10% ethanol, and 3-10% deionized water at room temperature for 30 minutes to 24 hours.

4. The method for making a bioprosthetic heart valve assembly of claim 1, wherein the method further comprising:
- g) detoxifying the glutaraldehyde from the treated tissue from the step f) of claim 1;
- h) dehydrating the tissue from the step g) using 60% to 95% of alcohol for one to eight hours at 25° C. to 55° C., wherein the alcohol is either ethanol or isopropanol;
- i) treating the tissue from the step h) with a solution consisting of 80-90% glycerol, 5-10% ethanol, and 3-10% deionized water at room temperature for 30 minutes to 24 hours;
- j) cutting leaflets from the treated tissue of the step i); and
- k) assembling the heart valve assembly using the cut leaflets.

* * * * *